(12) United States Patent
Kimble et al.

(10) Patent No.: US 6,465,799 B1
(45) Date of Patent: Oct. 15, 2002

(54) UV RADIATION SYSTEM HAVING MATERIALS FOR SELECTIVELY ATTENUATING RADIATION

(75) Inventors: Allan W. Kimble; John B. Enns; James A. Ebel, all of Jacksonville, FL (US)

(73) Assignee: Johnson & Johnson Vision Care, Inc., Jacksonville, FL (US)

(*) Notice: Subject to any disclaimer, the term of this patent is extended or adjusted under 35 U.S.C. 154(b) by 0 days.

(21) Appl. No.: 09/515,190

(22) Filed: Feb. 29, 2000

Related U.S. Application Data

(63) Continuation-in-part of application No. 09/259,758, filed on Mar. 1, 1999
(60) Provisional application No. 60/143,607, filed on Jul. 13, 1999.

(51) Int. Cl.$^7$ ............................................. A61L 12/26
(52) U.S. Cl. ............................. 250/504 R; 250/455.11
(58) Field of Search .................... 250/504 R, 504 H, 250/455.11; 422/24; 252/582, 588, 589; 501/64; 359/358, 361

(56) References Cited

U.S. PATENT DOCUMENTS

| | | | |
|---|---|---|---|
| 3,711,746 A | 1/1973 | King ........................... 317/258 |
| 3,817,703 A | 6/1974 | Atwood ........................... 21/2 |
| 3,907,439 A | 9/1975 | Zanoni ........................ 356/160 |
| 3,941,670 A | 3/1976 | Pratt, Jr. ....................... 204/158 |
| 3,955,921 A | 5/1976 | Tensmeyer ..................... 21/54 |
| 3,979,696 A | 9/1976 | Buchman ................. 331/94.5 P |
| 4,015,120 A | 3/1977 | Cole ........................... 250/216 |
| 4,042,325 A | 8/1977 | Tensmeyer ..................... 21/54 |
| 4,071,334 A | 1/1978 | Kolb et al. ....................... 55/2 |
| 4,077,782 A | 3/1978 | Drummond et al. ........... 55/139 |
| 4,236,900 A | 12/1980 | Fitch et al. .................... 55/138 |
| 4,349,359 A | 9/1982 | Fitch et al. .................... 55/151 |

(List continued on next page.)

FOREIGN PATENT DOCUMENTS

| | | | |
|---|---|---|---|
| DE | 19748098 A1 | 7/1999 | ............. A61L/2/10 |
| EP | 0 222 309 B1 | 2/1990 | ........... B65B/55/10 |
| EP | 0479723 B1 | 9/1991 | |
| EP | 0 277 505 B1 | 4/1992 | ............. A61L/2/10 |

(List continued on next page.)

OTHER PUBLICATIONS

"Medical Device Sterilization", 3–Day Seminar Apr. 27–29, 1998.

Bright Light Sterilization Test Protocol Report "Visibility Tinted UV Blocking Acuvue", Sep. 17, 1996.

(List continued on next page.)

*Primary Examiner*—Jack Berman
(74) *Attorney, Agent, or Firm*—Anne B. Kieman

(57) ABSTRACT

This invention provides a high energy radiation system which produces UV radiation comprising a selectively attenuating material which increases the ratio of desired to undesired radiation to reduce the radiation damage to a target by selectively attenuating at least 30 percent of the radiation from greater than 200 up to 240 nm which impinges upon said attenuating material, and directs greater than 50 percent of the radiation from 240 nm to 280 nm which impinges upon said attenuating material.

49 Claims, 5 Drawing Sheets

U.S. PATENT DOCUMENTS

| | | | |
|---|---|---|---|
| 4,464,336 A | 8/1984 | Hiramoto | 422/24 |
| 4,518,502 A | 5/1985 | Burns et al. | 210/634 |
| 4,524,079 A | 6/1985 | Hofmann | 426/234 |
| 4,591,724 A | 5/1986 | Fuse et al. | |
| 4,629,896 A | 12/1986 | Bridgen | |
| 4,695,472 A | 9/1987 | Dunn et al. | 426/237 |
| 4,734,917 A | 3/1988 | Johnson | 372/70 |
| 4,766,288 A | 8/1988 | Berkes et al. | 219/216 |
| 4,836,859 A | 6/1989 | Konishi et al. | 134/1 |
| 4,838,154 A | 6/1989 | Dunn et al. | 99/451 |
| 4,867,796 A | 9/1989 | Asmus et al. | 131/1 |
| 4,871,559 A | 10/1989 | Dunn et al. | 426/248 |
| 4,910,942 A | 3/1990 | Dunn et al. | 53/425 |
| 4,912,720 A | 3/1990 | Springsteen | 372/72 |
| 4,989,215 A | 1/1991 | Winik | 372/70 |
| 5,034,235 A | 7/1991 | Dunn et al. | 426/238 |
| 5,048,404 A | 9/1991 | Bushnell et al. | 99/451 |
| 5,120,499 A * | 6/1992 | Baron | 250/455.11 |
| 5,133,932 A | 7/1992 | Gunn et al. | 422/24 |
| 5,196,174 A | 3/1993 | Cerola et al. | 422/300 |
| 5,232,367 A | 8/1993 | Vassiliadis et al. | 433/224 |
| 5,235,905 A | 8/1993 | Bushnell et al. | 99/451 |
| 5,262,902 A * | 11/1993 | Okumura et al. | 250/504 R |
| 5,263,042 A | 11/1993 | Kojima et al. | 372/72 |
| 5,328,517 A | 7/1994 | Cates et al. | 134/7 |
| 5,364,645 A | 11/1994 | Lagunas-Solar et al. | 426/248 |
| 5,390,073 A | 2/1995 | McMillan | 361/327 |
| 5,393,541 A | 2/1995 | Bushnell et al. | 426/237 |
| 5,446,289 A * | 8/1995 | Shodeen et al. | 250/453.11 |
| 5,447,733 A | 9/1995 | Bushnell et al. | 426/237 |
| 5,489,442 A | 2/1996 | Dunn et al. | 426/248 |
| 5,512,123 A | 4/1996 | Cates et al. | 156/272.6 |
| 5,514,391 A | 5/1996 | Bushnell et al. | 426/237 |
| 5,581,573 A | 12/1996 | Tanuma | 372/72 |
| 5,618,492 A | 4/1997 | Auten et al. | 422/22 |
| 5,658,530 A | 8/1997 | Dunn | 422/24 |
| 5,688,475 A | 11/1997 | Duthie, Jr. | |
| 5,723,096 A | 3/1998 | Bruun-Jensen | 422/301 |
| 5,768,853 A | 6/1998 | Bushnell et al. | 53/167 |
| 5,786,598 A | 7/1998 | Clark et al. | 250/455 |
| 5,801,483 A | 9/1998 | Watanabe et al. | 313/485 |
| 5,900,211 A | 5/1999 | Dunn et al. | 422/24 |
| 6,013,918 A | 1/2000 | Bushnell et al. | 250/454.11 |

FOREIGN PATENT DOCUMENTS

| | | | |
|---|---|---|---|
| EP | 0 691 270 A2 | 1/1996 | B65B/55/02 |
| JP | 06077596 B2 | 10/1994 | |
| JP | 09-049923 A | 2/1997 | |
| JP | 10-160915 A | 6/1998 | |
| RU | 2001629 | 10/1993 | |
| RU | 2092191 | 10/1997 | |
| WO | WO 96/09775 | 4/1996 | A23L/3/00 |
| WO | WO 97/14915 | 4/1997 | F21V/29/00 |
| WO | WO 97/33629 | 9/1997 | A61L/2/00 |
| WO | WO 97/35624 | 10/1997 | A61L/2/10 |
| WO | WO 97/43915 | 11/1997 | |
| WO | WO 99/08137 | 2/1999 | G02B/1/04 |

OTHER PUBLICATIONS

Peter J. Dolman, M.D. and Michael J. Dobogowski, M.D. "Contact Lens Disinfection by Ultraviolet Light"—American Journal of Ophthalmology 108:665–669, Dec., 1989.

David C. Gritz, MD; Tae Y. Lee, MD; Peter J. McDonnell, MD; Katherine Shih, PhD; Neville Baron, MD "Ultraviolet Radiation for the Sterilization of Contact Lenses"—The CLAO Journal, vol. 16, No. 4 pp. 294–298—Oct., 1990.

Verinder S. Nirankari, MD FACS, "Sterilizing Contacts with Ultraviolet Light"; Science Writers Seminar.

Teruo Miyata, Takeshi Sohde, Albert L. Rubin and Kurt H. Stenzel; "Effects of Ultraviolet Irradiation on Native and Telopeptide–Poor Collagen"—Biochem Biophys, 229 1971; pp. 672–680.

Joseph Dunn, Thomas Ott, and Wayne Clark—"Pulsed–Light Treatment of Food and Packaging"Food Technology, a Publication of the Institute of Food Technologists The Society for Food Science and Technology—Sep. 1995, vol. 49, No. 9.

"Disinfection by UV–radiation"—Philips Lighting.

"Germicidal Lamps"—Teltech® Literature Search Service, Dec. 23, 1998.

"MicroPlasma™ ESF™ Optical Filters and Coatings"—Corning web site Dec. 22, 1998.

Warriner, K. et al., "Inactivation of *Bacillus subtilis* spores on packaging surfaces by u.v. excimer laser irradiation", *Journal of Applied Microbiology* 2000, 88, 678–685.

* cited by examiner

UV RADIATION SYSTEM HAVING MATERIALS FOR SELECTIVELY ATTENUATING RADIATION

This invention claims the benefit of earlier filed provisional application U.S. Serial No. 60/143,607 filed Jul. 13, 1999 having the same title, and further this application is a continuation in part of U.S. Ser. No. 09/259,758 titled "Method of Sterilization" filed Mar. 1, 1999. Both aforementioned applications are incorporated herein by reference.

FIELD OF THE INVENTION

This invention is directed to a UV radiation system having a material for increasing the ratio of desirable radiation to undesirable radiation to a target provided by a radiation source.

BACKGROUND OF THE INVENTION

In the field of UV sterilization or disinfection, the typical target media is a durable (non-absorbing, non-degenerating) material such as metal, ceramic or chemically simple solutions like water or saline, and the energies involved are typically low, that is, less than 0.1 J/cm$^2$ per pulse total radiation or 20 Watts/cm$^2$ for a continuous radiation source.

The use of a high energy broad spectrum radiation source to inactivate microorganisms has been disclosed in the prior art. U.S. Pat. Nos. 5,768,853; 5,786,598; 5,034,235; 4,871,559; and 5,900,211; and WO96/09775 have disclosed the use of a broad spectrum radiation source to inactivate microorganisms on food, water and medical devices. For the applications of the broad spectrum radiation source, damage to the exposed articles, such as the food, water, and medical devices by the radiation has not been considered. U.S. Pat. Nos. 5,768,853 and 5,900,211 suggest that the cooling fluid around the flash lamps can be replaced with a liquid for cooling and/or spectral filtering by the use of selected liquid solutions with desired spectral transmittance/absorbance characteristics. No materials other than water are suggested for the spectral filtering liquid, nor is there any discussion of which ranges to filter and/or for what purpose. U.S. Pat. No. 5,768,853 discloses that the outer safety glass of one of the described embodiments does filter out wavelengths shorter than 200 nanometers (nm) to prevent the formation of ozone outside the outer safety glass, although the composition of the glass is not disclosed.

WO 97/33629 discloses a method of sterilization and purification of biological sera and other contaminated fluids through the deactivation of pathogens by exposing them to a precise spectra of UV radiation. The precisely controlled spectra of radiation is specific to the molecular make-up of the pathogens to kill them, but leaves the surrounding cells, proteins, and other components intact. The biological sera are irradiated with UV radiation from about 200 nm to about 250 nm. The specific wavelengths that provide optimal kill of each virus, bacteria or other microorganism is determined within a narrow range of from 3.0 to about 10.0 nm, preferably 3 to 5 nm. A transmitter/regulator, grating or other optical filter can be used to control the wavelength size and variation, but there are no specific examples described. The exposure cell window where the sera is placed is made of quartz, sapphire or UV grad fused quartz silica and can be coated with a transmission material such as polytetrafluorocarbon which allows the UV radiation wavelength to pass through unadulterated. Teflon may also be used as a UV transparent disposable lining.

EPO 0277505 B1 discloses a UV radiation lamp, which is used for sterilizing bottles. The lamp has a reflector, referred to in the patent as a mirror which has a dielectric coating. The dielectric coating (dichroic or interference filter) is used to achieve selective reflection of UV radiation. The reflector can be coated with several tens of dielectric layers each having a thickness of a quarter of the wavelength of the radiation. Suitable materials for the dielectric coating include $AL_2O_3/NaF$, $Sc_2O_3/MgF_2$, $ThF_4/Na_2AlF_6$, $HfO_2/SiO_2$, and $PbF_2/Na_3AlF_6$. Dielectric coatings are suitable for low energy absorption of UV radiation, but will not survive the demands of a high energy system, and will have short effective lifetimes in a high energy system. Further, dielectric filters are extremely angle sensitive, so they will not be effective for a shaped reflector, which changes the angle of incidence at the filter.

Lamp manufacturers often add dopants to the lamp envelope in a lamp to extend the life of the lamp. Depending on the lamp and what it is to be used for, some dopants are selected to cut off UV radiation entirely, e.g. cerium oxide in the lamp envelope of flash lamps used in laser applications. Other dopants are selected to cut off that portion of the UV radiation less than 180 nm which creates ozone. Lamps having these dopants are called "ozone-free bulbs." Other dopants are added to the lamp envelope to strengthen the lamp envelope against thermal shock.

For the application of high energy UV radiation to a polymeric medical device, the inventors have determined that damage to the medical device due to the radiation exposure must be considered, because it may render the exposed medical device useless for its intended purpose. There is a need for materials and ways to incorporate the materials into the lamp system to attenuate the undesirable portion of the UV radiation which is damaging to the polymeric medical device without reducing or significantly reducing the desired portion of the UV radiation, e.g. germicidal effective radiation.

SUMMARY OF THE INVENTION

This invention provides a high energy radiation system which produces UV radiation comprising a selectively attenuating material which increases the ratio of desired to undesired radiation to reduce the radiation damage to a target by selectively attenuating at least 30 percent of the radiation from 180 up to 240 nm which impinges upon said attenuating material, and directs greater than 50 percent of the radiation from 240 nm and 280 nm which impinges upon said attenuating material.

The radiation system comprising attenuating materials which selectively attenuate the radiation make it possible to expose to high energy UV radiation targets which are sensitive to UV radiation from 180 nm up to 240 nm. These high energy UV radiation systems produce radiation, which is undesired and desired. Without attenuation, the undesired UV radiation damages the materials of or changes the characteristics of a target at the same time the desired UV radiation is delivered. The target can be any material which comprises UV-sensitive composition(s). Damage to the target includes color changes of organic or inorganic dyes, chain scissions or alteration of the mechanical properties of polymers or other organic materials, or causing oxidation of organic materials. By selectively attenuating the undesired radiation, it is possible to use a high energy UV radiation system on products including organic products and inorganic products which would otherwise be damaged by the radiation, or to treat a broader class of materials, some of which have a low threshold for damage when subjected to the undesired radiation. This invention also simplifies the process control for the radiation systems used to expose UV-sensitive targets, because the amount of undesired radiation delivered after attenuation can be tailored to be below or much below the threshold for damage to the target, which will give more leeway in the amount of radiation which can be delivered. In the preferred embodiments, this invention is used to treat polymeric contact lenses in solution in polymeric packaging. The UV radiation damages the contact lens polymers, container polymers and solution additives. The invention will be described in reference to polymeric target materials; however, it is understood that additional UV-sensitive target materials could be treated by the method of this invention. One important application for this invention is in a lamp system for lasers wherein the target material is the laser medium, e.g. laser dyes, or other organic medium, which is sensitive to UV radiation.

DETAILED DESCRIPTION OF THE INVENTION

Figure 1:
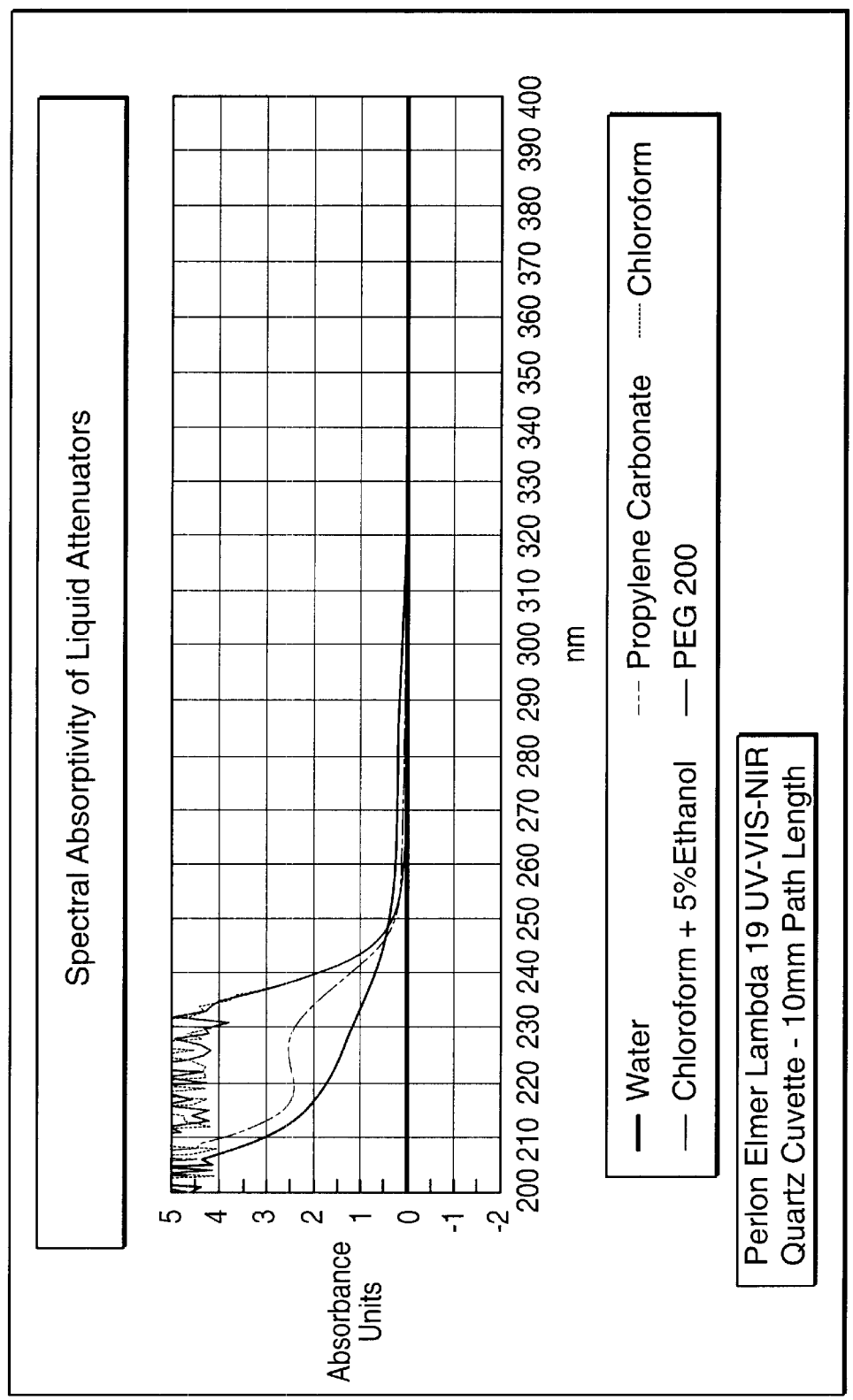
FIG. 1 is a graph of absorbance per wavelength for various liquid attenuating materials useful in this invention.

The radiation system of this invention comprises a high energy UV radiation source. UV radiation sources that can be used in the radiation system include discrete or continuous producing, incoherent lamps, such as flash lamps, arc lamps (continuous or non-continuous), deuterium lamps, or continuous wave light sources, e.g. xenon gas or mercury vapor light sources. The UV radiation sources are high energy, that is, they generate greater than 0.1 $J/cm^2$ per pulse for a flash lamp or 20 watts/$cm^2$ for a continuous radiation source, preferably of which at least 1 percent of the radiation is from 240 to 280 nm. The presently preferred UV radiation source is a flash lamp which produces at least 1 $J/cm^2$ broad spectrum radiation (200–3000 nm) per flash of which at least 10 $mJ/cm^2$ per flash is UV radiation. The preferred application is sterilization, in particular sterilization of contact lenses (target). For sterilization, the desired radiation is the germicidal radiation which includes the radiation from 240 to 280 nm; with many references indicating that 254 nm is the peak of the germicidal range; however, destruction to the contact lens polymer occurs upon exposure to the radiation below 320 nm to about 100 nm (non-ionizing UV radiation). U.S. Ser. No. 09/259,758, titled "Method of Sterilization", earlier incorporated by reference, discloses that radiation at wavelengths less than 320 nm are absorbed by the contact lens polymers and may cause chain scissions within the polymers. The most destructive radiation is from 180 nm up to 240 nm. (The term "up to" when used to describe a range means that the endpoint is not included within the range specified.) To prevent the destruction to polymers of the target, e.g. container or medical device by chain scissions or other mechanisms due to the UV radiation, this invention provides attenuating materials and ways of incorporating the attenuating materials into the radiation system to attenuate the undesirable wavelengths from at least a portion of the destructive radiation dose before the radiation reaches the target. U.S. patent application Ser. No. 09/259,758, further discloses that the energy of the radiation (240 to 280 nm) to the microorganism has to be at least 18 $mJ/cm^2$ for sterilization.

To protect the polymeric target, it is preferred to attenuate the radiation or a portion of the radiation from 180 nm up to 240 nm; or at least greater than 200 nm up to 240 nm. However, for some applications it may be more preferable to attenuate the radiation or a portion of the radiation from 180 nm up to 250 nm. To attenuate the undesired radiation to protect the polymeric target from damage and to prevent the formation of ozone, it is beneficial to attenuate the undesired radiation from 100 nm up to 240 nm. Ideally 100 percent of the total radiation at the undesired wavelengths would be attenuated; however, even small percentages of attenuation of ranges of wavelengths of the undesired radiation are beneficial, because the attenuation increases the ratio of the desired (e.g. germicidally-effective) radiation to the undesired (e.g. damaging) radiation reaching the target, e.g. polymer, container and/or product. Increasing the ratio of germicidally-effective radiation to damaging radiation makes it possible to increase the overall radiation dose, if necessary for sterility, and makes it easier to control the system when the threshold of damage to the polymer is far below the dose for sterility.

It is preferred that the attenuating materials of this invention provide greater than a 30 percent reduction in the total undesired radiation, more preferably greater than a 60 percent reduction, and most preferably greater than a 90 percent reduction in the total undesired radiation which impinges upon the attenuating materials. For the preferred embodiments, the undesired radiation is from 100 nm up to 240 nm, or at least from 180 nm up to 240 nm, or at least greater than 200 nm up to 240 nm. It is preferred to attenuate at least a portion of all the wavelengths of radiation specified in the specified ranges. Typically, the attenuating materials will not attenuate all the wavelengths in a given range at a single percentage, so certain attenuating materials will be better suited for some applications than others, or mixtures of the attenuating materials can be used to achieve improved reductions at certain or all of the wavelengths in the range of undesired wavelengths. An example of a mixture is chloroform and absolute ethanol. It is preferred that the attenuating materials attenuate the undesired radiation, and that the attenuating materials direct the desired radiation toward the target. The attenuating materials can direct the desired radiation toward the target by transmitting and/or reflecting the desired radiation from the radiation source which impinges upon the attenuating material, and/or by re-emitting absorbed undesired radiation as radiation within the desired radiation. The attenuating materials can direct the desired radiation towards the target either directly or indirectly, that is, the desired radiation may impinge upon other apparatus before striking the target, e.g. reflectors, mirrors, fiber optics, or the like. Preferably the attenuating materials direct greater than 50 percent of the desired radiation, more preferably greater than 75 percent and most preferably greater than 90 percent of the desired radiation, which impinges upon the attenuating materials. For sterilization the desired radiation is 240 to 280 nm. (Whether the attenuating materials direct, e.g., transmit, reflect and/or re-emit, the desired radiation to the target can determine where the attenuating materials are positioned with respect to the radiation source and target.) Preferably, at least a portion of all the wavelengths of the undesired radiation in the ranges specified is transmitted, reflected or emitted by the attenuating materials. The preferred materials are those that attenuate greater than 30 percent of the undesired radiation and direct greater than 50 percent of the desired radiation. The more preferred attenuating materials attenuate greater than 50 percent of the total radiation from 100 up to 240 nm and direct greater than 90 percent of the total radiation from 240 to 280 nm which impinges upon the attenuating materials whereby at least some portion of the radiation between 200 up to 240 nm is attenuated, preferably greater than 30%, more preferably greater than 60%, most preferably greater than 90% of the radiation between 200 up to 240 nm is attenuated. Preferably, at least a portion of all the wavelengths of the undesired radiation in the ranges specified is attenuated, and at least a portion of all the wavelengths of the desired radiation in the ranges specified is directed.

The attenuation materials preferably provide an attenuation ratio greater than 1.2, more preferably greater than 1.8, most preferably greater than 2.5. The attenuation ratio is defined as the percent of the desired radiation directed by the attenuation materials divided by the percent of the undesired radiation absorbed by the attenuation materials. For example, the attenuation ratio of a reflector of lanthanum oxide would have an attenuation ratio of 3 (see Table 1).

Attenuating materials can be liquids, solids, or gases. An example of an attenuating material which is a gas is ozone, e.g. 10 ppm ozone in air. Liquid attenuating materials include polyols, such as alkyl alcohols, more preferably propylene glycols having a weight average molecular weight from 200 to 1,000, and most preferably propylene glycols having a weight average molecular weight of 200. Examples of polyethylene glycols include PEG 200, PEG 400, PEG 600, from Aldrich Chemical Co. Other useful liquid attenuating materials are halogenated carbon compounds, such as, fluorocarbons, chlorocarbons, chloroform, more preferably fully halogenated carbon compounds, because they are more stable, such as, freon, except for fluorinerts which are also more preferred although not fully halogenated. Examples of fluorinerts include FC-40, FC43, FC-70, commercially available from 3M, available from Aldrich Chemical Company. The preferred fluorinerts have nitrogen within their compositions. Other liquid attenuating materials include organic carbonates, more preferably aliphatic carbonates, such as propylene carbonates. Other useful liquid attenuating materials include silicon compounds, such as sodium silicate, more preferably polysiloxane compounds such as polydimethylsiloxanes, most preferably hydride-terminated silicone oil. Mixtures of the above-described liquids can be used as the liquid attenuating materials. The preferred mixtures are those of halogenated carbon compounds and organic carbonates, more preferably chloroform and propylene carbonate. Ways to incorporate the liquid attenuating materials into the radiation system to attenuate radiation will be described below. Typically the liquid attenuating materials will need to be pumped through or around the radiation source or target of the radiation; therefore, it is preferred that the liquid attenuating materials have a viscosity from 1 to 1,000 cps, more preferably from 1 to 500 cps and most preferably from 1 to 100 cps. The easiest liquid attenuating materials to pump have a viscosity of from 1 to 10 cps. The liquid attenuating materials can be used in a suitable liquid carrier; preferably a non-ionic liquid, or they can comprise a solid attenuating material in a suitable liquid carrier to form a dispersion or colloid with the solid, for example 2-hydroxyethylmethacrylate (HEMA) or ethylene glycol dimethacrylate (EDGMA) in water.

Examples of liquids which can be used as attenuating materials are shown in FIG. 1. The curves in FIG. 1 were generated by placing cuvettes having a 10 mm pathlength filled with the sample liquids into a spectrophotometer, and recording the light which passed through the samples.

Figure 2:
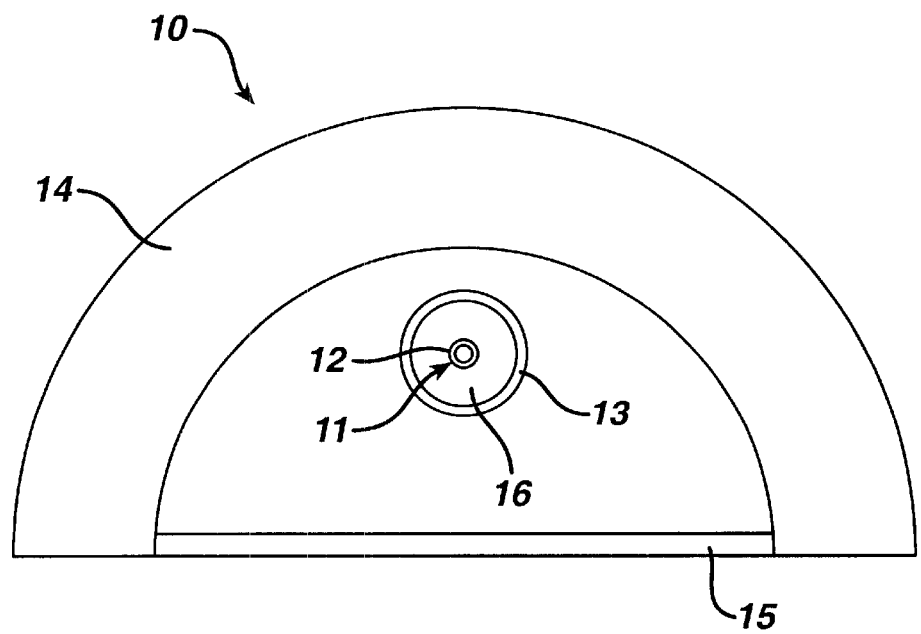
FIG. 2 shows a cross-section of a flash lamp of this invention having an attenuating material.

Liquid attenuating materials can be used in various locations to attenuate selected radiation. A first set of embodiments using liquid attenuating materials will be described in reference to FIG. 2. FIG. 2 shows a cross-section of a conventional flash lamp 10; although it is understood that other radiation sources described earlier can be used in the radiation system of this invention, such as arc lamps (continuous or non-continuous), deuterium lamps, or any other source which produces at least a portion of the radiation from 180 up to 240 nm or greater than 200 up to 240 nm, and at least a portion of the radiation from 240 to 280 nm, and most preferably in a continuum between 100 and 400 nm. The flash lamp 10 consists of a lamp 11 which consists of two electrodes (not shown) each connected to the end of a hollow lamp envelope 12. The lamp envelope 12 is made out of a strong transparent material which can withstand high temperatures and thermal shock such as glass, quartz or sapphire or the like. The lamp generates radiation when an arc is created between the electrical connectors. The lamp envelope 12 may be inside a flow tube 13 as shown. The flow tube 13 provides protection for the lamp envelope 12. Typically cooling water is pumped in the passageway 16 formed between the lamp envelope 12 and the flow tube 13 to dissipate the heat generated by the lamp 11. In one embodiment of the invention one or more liquid attenuating materials can be used in place of the cooling water in the passageway 16 between the flow tube 13 and the lamp envelope 12 to both attenuate selected wavelengths and to cool the lamp 11. In this embodiment the attenuating materials can be pumped in the passageway 16 between the lamp envelope 12 and the flow tube 13. Attenuating materials pumped between the lamp envelope and the flow tube must be highly resistive, preferably greater than 1 megohm, more preferably greater than 10 megohms, most preferably greater than 18 megohms, because of the potential of a short circuit within the lamp.

Figure 3:
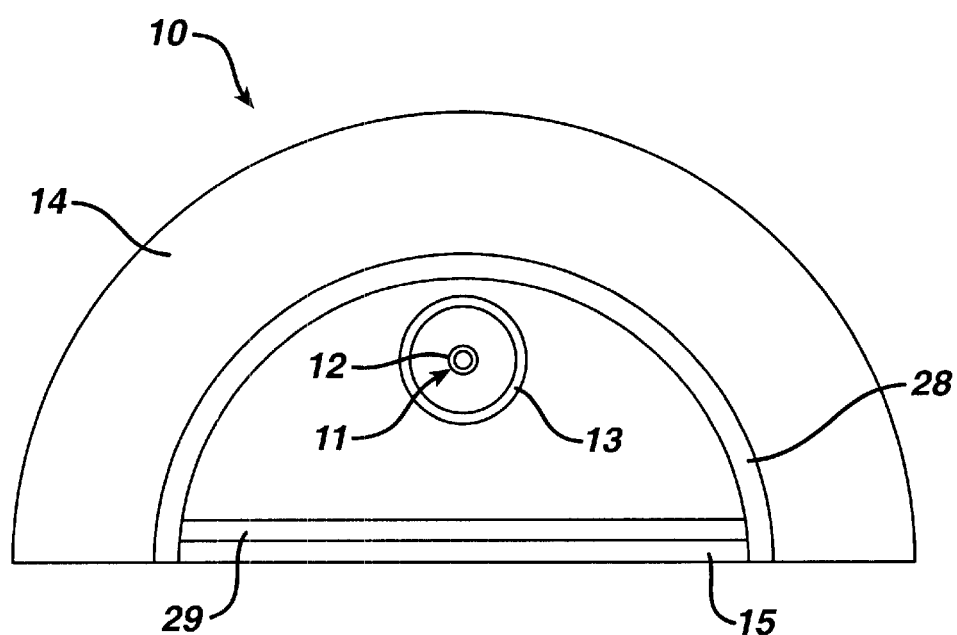
FIG. 3 shows a cross-section of another flash lamp of this invention having an attenuating material.

Another embodiment of the invention is shown in FIG. 2. The flash lamp 10, in FIG. 3 is similar to the flash lamp shown in FIG. 2 and consists of a reflector 14, and a protective window 15 (similar elements are labeled with the same number in the figures). Passageways 28 and 29 may be added adjacent to the reflector 14 or the protective window 15 through which liquid attenuating materials may be added or pumped and used to attenuate selected wavelengths of the radiation. The passageways may be constructed of glass, quartz, sapphire or the like. Both passageways 28, 29 are shown in FIG. 3, but in alternative embodiments each passageway 28 or 29 may be used alone to hold an attenuating material to attenuate the undesired radiation.

The sensitivity of the liquid attenuating materials to the radiation will determine the exposure amounts of the liquid attenuating materials to the radiation. If the liquid attenuating materials ability to absorb or otherwise attenuate the radiation breaks down significantly after one exposure to the radiation, then those liquid attenuating materials can be continuously pumped through the passageways, exposed only once to the radiation, and then discarded. If the sensitivity to the radiation is less, then the liquid attenuating materials can be exposed to several flashes and then discarded, or exposed once to the radiation and mixed with a reservoir of the liquid attenuating material from which additional liquid attenuating material can be drawn and exposed, and this process can be repeated for an amount of time until it is determined that the ability of the liquid attenuating material in the reservoir to attenuate the radiation has been reduced to a point that the reservoir should be discarded and replaced with a fresh supply of liquid attenuating material. The attenuation ability of the liquid attenuating materials can be monitored using a spectrophotometer. The composition of the passageways in which the liquid attenuating materials are held and the individual liquid attenuating material's ability to attenuate the undesired radiation will be factors to consider when determining the thickness of the passageways (wavelength pathlength) which hold the liquid attenuating materials.

Solid attenuating materials include, but are not limited to, alkaline metal compounds (oxides and halides), heavy metal oxides (e.g. barium), divalent metal oxides (e.g. magnesium), and polyvalent metal oxides (e.g. ytterbium or aluminum). Solid attenuating materials can also be selected according to the following formula $M_aO_bX_cH_d$ wherein M is a single metal or a mix of metals, preferably a rare earth metal, O is oxygen, X is a heteroatom such as sulfur, nitrogen and phosphorous or the like, and H is a halide, preferably fluorine, a is 1 to 20, preferably 1 to 12, b is 0 to 20, preferably 0 to 12, c is 0 to 20, preferably 0 to 12, and d is 0 to 20, preferably 0 to 12, with the proviso that at least b, c or d is at least 1. These materials need to be of sufficient purity such that the levels of impurities do not degrade the reflector performance. Preferably the materials are more than 99.9% pure, more preferably more than 99.99% pure. Examples of useful solid materials are listed in Table 1. Included in Table 1 are the mean percent reflectivites of the solid attenuating materials. The percent reflectivities were determined by packing a dry powder sample of solid material into a cuvette, and putting the cuvette into a spectrophotometer having an integrating sphere which measured the radiation reflected from the sample.

TABLE 1

Attenuating Materials

| Material | Observed Visual Color | % R Mean 200–400 | % R Std Dev 200–400 | % R Mean 240–280 | % R Std Dev 240–280 | % R Mean 200–240 | % R Std Dev 200–240 |
|---|---|---|---|---|---|---|---|
| Barium Titanate | Beige | 18.55 | 10.11 | 14.42 | 0.27 | 21.44 | 9.04 |
| Cerium Oxide | Beige | 62.69 | 26.63 | 55.84 | 18.08 | 23.08 | 11.18 |
| Erbium Oxide | Pink | 62.69 | 26.63 | 55.84 | 18.08 | 23.08 | 11.18 |
| Europium Oxide | White | 54.79 | 34.3 | 45.1 | 1.26 | 23.78 | 10.73 |
| Germanium Dioxide | White | 84.13 | 21.32 | 72.83 | 10.51 | 50.72 | 14.64 |
| Hafnium Oxide | Beige | 32.26 | 7.49 | 25.83 | 0.51 | 31.04 | 9.69 |
| Holmium Oxide | Pink | 66.75 | 27.37 | 67.18 | 20.46 | 20.88 | 9.31 |
| Lanthanum Oxide | White | 82.99 | 28.39 | 88.23 | 11.97 | 29.49 | 12.36 |
| Magnesium Oxide | White | 97.27 | 14.21 | 101.44 | 0.52 | 19.68 | 24.49 |
| Praseodymium Oxide | Black | 13.67 | 5.59 | 12.13 | 0.33 | 20.7 | 9.49 |
| Samarium Oxide | L. Yellow | 68.84 | 27.62 | 51.32 | 23.08 | 27.58 | 6.59 |
| Terbium Oxide | Brown | 13.11 | 6.09 | 11.55 | 0.58 | 21.15 | 9.99 |
| Titanium Dioxide | White | 14.92 | 5.17 | 13.12 | 0.28 | 20.75 | 9.14 |
| Ytterbium Oxide | White | 70.72 | 33.16 | 45.8 | 26.02 | 23.2 | 11.84 |
| Yttrium Oxide | White | 85.81 | 24.14 | 89.38 | 6.51 | 41.14 | 15.4 |
| Zinc Oxide | White | 15.85 | 13.39 | 10.99 | 0.35 | 20.72 | 11.36 |

In the formula for the solid attenuating materials, when a is 1 to 6 and b is 1 to 11, and c and d are 0 then the solid attenuating material is a metal oxide, such as calcium oxide (CaO) and hafnium oxide ($HfO_2$), lanthanum oxide ($La_2O_3$), iron oxide ($Fe_3O_4$), terbium oxide ($Tb_4O_7$), praseodymium oxide ($Pr_6O_{11}$), and barium titanate ($BaTiO_3$). An example of solid attenuating material for which a is 1, d is 2 and b and c are 0 is magnesium fluoride ($MgF_2$). Additional examples of solid attenuating materials include magnesium oxide (MgO), aluminum oxide ($Al_2O_3$) barium oxide (BaO), barium titanate ($BaTiO_3$), holmium oxide ($Ho_2O_3$), calcium oxide (CaO), lanthanum oxide ($La_2O_3$), germanium oxide ($GeO_2$), tellurium oxide ($TeO_2$), europium oxide ($Eu_2O_3$), erbium oxide ($Er_2O_3$), neodymium oxide ($Nd_2O_3$), samarium oxide ($Sm_2O_3$), ytterbium oxide ($Yb_2O_3$), yttrium oxide ($Y_2O_3$), and dysprosium oxide ($Dy_2O_3$). Other examples include refractory oxides of other rare earths, rare earth halides, and metallic combination oxides. The preferred attenuating materials are magnesium oxide, erbium oxide, holmium oxide, samarium oxide, tellurium oxide, lanthanum oxide, yttrium oxide, and ytterbium oxide, and the most preferred are lanthanum oxide, yttrium oxide, and ytterbium oxide.

The solid attenuating materials can be incorporated into the radiation source (e.g. a lamp envelope, protective window or flow tube) which prevents the damaging radiation from reaching the target, e.g. polymer, product and/or packaging, to be exposed. As stated earlier, examples of a radiation source include a pulsed light source (e.g. xenon gas) or a continuous wave light source (e.g. mercury vapor). The solid attenuating materials can be added to the feed stock used to make the glass (e.g. sapphire, quartz, glass, crystalline materials, and the like), as what is commonly referred to in the glass industry as a dopant, during the manufacture of the lamp envelope and/or the flow tube and/or protective window. Additionally, the proper selection of dopants for the flow tube or the lamp envelope can increase the performance of the lamp by reducing thermal shock, solarization, fluorescence, phosphorescence, and/or can be used to reduce the undesirable radiation by absorption, or absorption and re-emission at desired or at least not undesired wavelengths. Attenuating materials which can absorb radiation at undesired wavelengths and re-emit at desired wavelengths are preferred.

The attenuating materials can also be used to form a filter through which the radiation will pass prior to impinging upon the target which will attenuate the undesirable wavelengths before they contact the target, or the attenuating materials can be added to the packaging material. These embodiments will be described in more detail below.

To approximate the amount of dopant to add to the glass, quartz or sapphire flow tube, lamp envelope or protective window or for the formation of a filter or the packaging material through which the radiation will pass prior to impinging upon the polymeric target, and for other embodiments described below, the Beer-Lambert equation quantifies the radiation absorption by a particular dopant or attenuating material:

$$I(\lambda)/I_0(\lambda)=\exp(-\alpha(\lambda)cx)$$

where $I(\lambda)$ is the intensity of the attenuated radiation as a function of wavelength ($\lambda$), $I_0(\lambda)$ is the initial radiation intensity as a function of wavelength, $\alpha(\lambda)$ is the molar absorptivity of the dopant (attenuation material) as a function of wavelength, c is the concentration of the dopant, and x is the path length (thickness of the material in which the dopant is present) through which the radiation passes. $\alpha(\lambda)$ can be determined spectrophotometrically as described for generating the data in Table 2 or in a like way.

Figure 4:
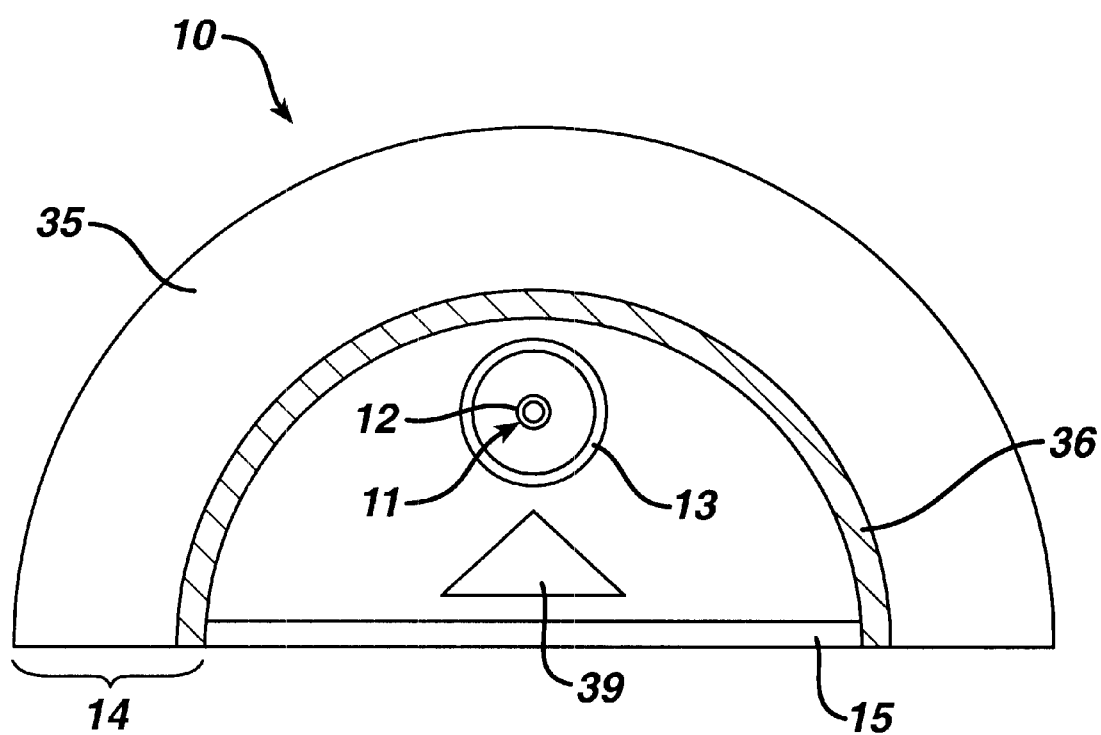
FIG. 4 shows a cross-section of another flash lamp of this invention having an attenuating material.
Figure 5:
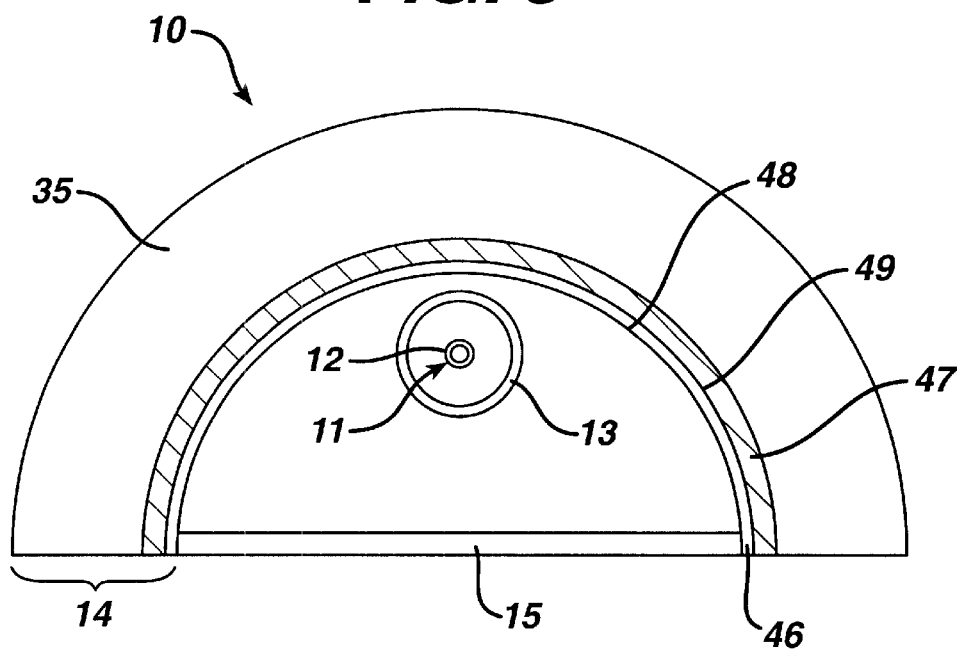
FIG. 5 shows a cross-section of another flash lamp of this invention having an attenuating material.

An alternative embodiment of the invention is to add the solid attenuating materials to other parts of the radiation source, e.g. as part of a reflector as described in reference to FIGS. 4 and 5. In FIG. 4 is shown a cross-section of a flash lamp 10 similar to that shown in FIG. 2 (similar elements are labeled with the same number). FIG. 4 shows an attenuating coating 36 as part of the reflector 14. The reflector 14 also consists of a reflector support 35. The attenuating coating 36 comprises an attenuating material. The attenuating coatings can be applied by painting, spraying, plasma coating, dipping, casting, conversion coating, gel coating, etching, chemical vapor depositing, sputtering, or chemical or mechanical bonding, e.g. by adhesives of a film comprising the attenuating materials to a reflector support 35. The preferred method of applying the attenuating coatings is to paint or spray attenuating materials onto a reflector support. To paint or spray them onto the support 35, an aqueous or non-aqueous suspension is formed preferably comprising attenuating material and binder. Useful binders are polymeric, inorganic or sol-gels, more preferably inorganic or sol gel, and most preferably inorganic. The preferred suspension comprises 0.1 to 50% binder, 0.1 to 99.9% attenuating material, and 0.1 to 90% carrier. The carrier is a liquid used to form a dilution of the attenuating materials and binder to apply the coating. Examples of useful carriers are water, alcohols, alkanes, freons, and the like, most preferably water.

Examples of polymeric binders useful in making coatings comprising attenuating materials are polyvinyl alcohols, cyanoacrylates, acrylics, and silicones. Presently the polymeric binders are limited in their use, because they tend to degrade in the high energy UV radiation. Examples of inorganic binders useful in making coatings comprising attenuating materials are sodium silicate, low-temperature sintered glasses, alkali oxide silicates, such as sodium, potassium and lithium silicates. Examples of sol gel binder precursors useful in making coatings comprising attenuating materials are aluminum tert butoxide, sodium silicate, tetraethylorthosilicate (TEOS), metal isopropoxides, dysprosium ethylhexano-diisopropoxide in isopropanol, dysprosium 2-ethylhexanoate in hexane, dysprosium isopropoxide in toluene-isopropanol, dysprosium 2-methoxyethoxide in 2-methoxyethanol, erbium ethylhexano-diisopropoxide in isopropanol, erbium 2-ethylhexanoate in hexane, erbium isopropoxide in toluene-isopropanol, holmium ethylhexano-diisopropoxide in isopropanol, holmium isopropoxide in toluene-isopropanol, holmium 2-methoxyethoxide in 2-methoxyethanol, lanthanum acetate, lanthanum 2-ethylhexanoate in hexane, lanthanum isopropoxide, lanthanum 2-methoxyethoxide in 2-methoxyethanol, magnesium ethoxide in ethanol, magnesium methoxide in methanol, magnesium 2-methoxyethoxide in 2-methoxyethanol, neodymium ethylhexano-diisopropoxide in isopropanol, neodymium 2-ethylhexanoate in hexane, neodymium isopropoxide in toluene-isopropanol, neodymium 2-methoxyethoxide in 2-methoxyethanol, samarium ethylhexano-monoisopropoxide in toluene isopropanol, samarium 2-ethylhexanoate in hexane, samarium isopropoxide in toluene-isopropanol, samarium 2-methoxyethoxide in 2-methoxyethanol, ytterbium isopropoxide in toluene-isopropanol, ytterbium 2-methoxyethoxide in 2-methoxyethanol, yttrium ethylhexano-diisopropoxide in toluene-isopropanol, yttrium ethylhexano-monoisopropoxide in toluene-isopropanol. The preferred sol gel precursors are erbium ethylhexano-diisopropoxide in isopropanol, erbium 2-ethylhexanoate in hexane, erbium isopropoxide in toluene-isopropanol, holmium ethylhexano-diisopropoxide in isopropanol, holmium isopropoxide in toluene-isopropanol, holmium 2-methoxyethoxide in 2-methoxyethanol, lanthanum acetate, lanthanum 2-ethylhexanoate in hexane, lanthanum isopropoxide, lanthanum 2-methoxyethoxide in 2-methoxyethanol, magnesium ethoxide in ethanol, magnesium methoxide in methanol, magnesium 2-methoxyethoxide in 2-methoxyethanol, samarium ethylhexano-monoisopropoxide in toluene isopropanol, samarium 2-ethylhexanoate in hexane, samarium isopropoxide in toluene-isopropanol, samarium 2-methoxyethoxide in 2-methoxyethanol, ytterbium isopropoxide in toluene-isopropanol, ytterbium 2-methoxyethoxide in 2-methoxyethanol, yttrium ethylhexano-diisopropoxide in toluene-isopropanol, yttrium ethylhexano-monoisopropoxide in toluene-isopropanol. The more preferred sol gel precursors are lanthanum acetate, lanthanum 2-ethylhexanoate in hexane, lanthanum isopropoxide, lanthanum 2-methoxyethoxide in 2-methoxyethanol, ytterbium isopropoxide in toluene-isopropanol, ytterbium 2-methoxyethoxide in 2-methoxyethanol, yttrium ethylhexano-diisopropoxide in toluene-isopropanol, yttrium ethylhexano-monoisopropoxide in toluene-isopropanol.

Some of the binders can be used alone as the attenuating materials, particularly the sol gels which can be applied as described above in a suspension or sintered to form a solid attenuating material. Examples of binders which can be used alone as the attenuating materials include dysprosium isopropoxide, dysprosium ethylhexano-diisopropoxide in isopropanol, dysprosium 2-ethylhexanoate in hexane, dysprosium isopropoxide in toluene-isopropanol, dysprosium 2-methoxyethoxide in 2-methoxyethanol, erbium ethylhexano-diisopropoxide in isopropanol, erbium 2-ethylhexanoate in hexane, erbium isopropoxide in toluene-isopropanol, holmium ethylhexano-diisopropoxide in isopropanol, holmium isopropoxide in toluene-isopropanol, holmium 2-methoxyethoxide in 2-methoxyethanol, Lanthanum acetate, Lanthanum 2-ethylhexanoate in hexane, Lanthanum isopropoxide, Lanthanum 2-methoxyethoxide in 2-methoxyethanol, Magnesium ethoxide in ethanol, Magnesium methoxide in methanol, Magnesium 2-methoxyethoxide in 2-methoxyethanol, Neodymium ethylhexano-diisopropoxide in isopropanol, Neodymium 2-ethylhexanoate in hexane, Neodymium isopropoxide in toluene-isopropanol, Neodymium 2-methoxyethoxide in 2-methoxyethanol, Samarium ethylhexano-monoisopropoxide in toluene isopropanol, Samarium 2-ethylhexanoate in hexane, Samarium isopropoxide in toluene-isopropanol, Samarium 2-methoxyethoxide in 2-methoxyethanol, Ytterbium isopropoxide in toluene-isopropanol, Ytterbium 2-methoxyethoxide in 2-methoxyethanol, yttrium ethylhexano-diisopropoxide in toluene-isopropanol, Yttrium ethylhexano-monoisopropoxide in toluene-isopropanol.

The attenuating materials disclosed herein can be used in thin layers and/or multiple layers of different attenuating materials similar to dichroic filters also referred to dielectric filters; however, the attenuating materials disclosed herein do not work by the same mechanism as a dielectric filter, that is, they do not rely upon a structure comprised of alternating materials with differing indices of refraction. The materials of this invention use absorption mechanisms to selectively attenuate the radiation.

The attenuating coatings are preferably applied to form a coating having a thickness from 0.1 to 2500 microns, more preferably a thickness from 0.5 to 2500 microns. (A coating greater than 2500 microns is considered a block of the material). The coatings are preferably applied in multiple layers of the same attenuating material(s), preferably in the same coating composition. The coating of the attenuating materials on a reflector reduces the undesired radiation which impinges upon the attenuating materials two times: once on the radiation's way to the reflector and once after the radiation is reflected off the reflector, which is a factor to consider when formulating the attenuating materials to be applied to the reflector, and when estimating the useful life of the attenuating materials (particularly if liquid attenuating materials are in a passageway in front of the reflector). Also, depending upon the shape of the one or more reflectors of the radiation source, much of the radiation will be reflected off of the reflectors multiple times before it reaches the target.

The reflector 14 which comprises the coating 36 of the attenuating material can comprise a reflective material, or a non-reflective or reflective reflector support 35 onto which a reflective coating (which may be a film or foil) is held. An example of a reflective material is metal. An example of a reflective reflector support 35 is a solid polished aluminum, which is thick enough to hold its shape, and is bolted or otherwise mounted into place around the lamp 11.

Other examples of reflective materials which can be used alone as the reflector support 35 include: formed solids of barium sulfate, aluminum oxide, magnesium fluoride, and magnesium oxide. The formed solids can be formed by combining the reflective materials with metal oxides or powdered glass and sintering them to form a reflective support, or by combining the reflective materials with binders and forming a solid either in the shape of the support or machining the reflector out of the resulting formed solid. Other examples of coatings of reflective material which can be applied, or otherwise attached to a reflective or non-reflective reflector support 35 include: magnesium oxide, magnesium fluoride, barium sulfate and aluminum oxide, including thin sheets of aluminum, aluminum oxide, magnesium fluoride, barium sulfate and magnesium oxide which can be attached to a reflector support 35. These coatings or films can be formed by sintering the reflective materials with glass compositions, or forming films of the reflective materials with binders. Examples of materials which can be used as a non-reflective reflector support 35 include: wood, polymers, metals and ceramics.

The reflective coatings of the reflector support 35 can be coated by painting, plasma coating, spraying, dipping, casting, conversion coating, gel coating, etching, chemical vapor deposition, sputtering, or mechanical or chemical bonding of a thin film or foil of the reflective material to a reflective or non-reflective support. The preferred method of applying the reflective materials which are part of the reflector 14 is to paint or spray them onto a reflector support 35. To paint or spray them onto the support 35, an aqueous or non-aqueous suspension is formed with a binder. The preferred binders are polymeric, inorganic or a sol-gel, more preferred inorganic or sol gels. Examples of polymeric binders are polyvinyl alcohols, cyanoacrylates, acrylics, and silicones. Presently the polymeric binders are the least preferred, because it is believed that the UV radiation will cause them to degrade. Examples of inorganic binders are sodium silicate, low-temperature sintered glasses, alkali oxide silicates, such as sodium, potassium and lithium silicates. Examples of sol gel precursors are listed above for the attenuating materials.

An example of an attenuating coating composition is 1 part sodium silicate (binder), 10 parts lanthanum oxide (attenuating material) and 10 parts water (carrier). 10 layers of this suspension were sprayed onto a reflector which comprised an aluminum substrate (reflector support) having a barium sulfate coating (reflective material). The barium sulfate coating was made by spraying 20 layers of a composition comprising 1 part sodium silicate (binder), 10 parts barium sulfate (reflective material) and 10 parts water (carrier) onto the aluminum substrate. Each coating was air dried between coatings.

In an alternative embodiment, the reflective materials and attenuating materials and optional binders can be combined and applied to a reflective or non-reflective reflector support 35 in a single coating which reflects the desired, e.g. germicidally-effective radiation, and attenuates the undesired radiation. The attenuating materials may act as the binder for the reflective material, therefore eliminating the need for a binder in the composition. Examples of materials which can act as the binder and attenuating material are dysprosium isopropoxide, polysiloxanes, and all the sol gels, listed above. The attenuating material and reflective material can be sintered to form a reflector coating 36 composition having radiation attenuating properties. An example of a material which can be used as a sintering material is a low melting glass composition, to which the attenuating material and reflective materials can be added. These coatings preferably have a thickness between 0.1 and 2500 microns.

Alternatively, a reflector 14, similar to the one shown in FIG. 1, can be formed out of a formed solid comprising attenuating materials, reflective material, and optional binders. The composition is formed in the shape of a reflector 14 or the reflector 14 can be machined out of the formed solid which comprises the reflector materials, attenuating materials and optional binders. Further, the attenuating materials can be combined with metal oxides or powdered glass and reflective materials and sintered to form a reflector 14 similar to the one shown in FIG. 1 which has attenuating and reflective properties. The just-described formed solids preferably have a thickness greater than 2500 microns.

Presently it is not preferred to combine the reflective materials with the attenuating materials, because the radiation at undesired wavelengths may be reflected by the reflective materials before the attenuating materials have an opportunity to absorb the undesired wavelengths.

The preferred attenuating materials are those that absorb the undesired radiation from 100 up to 240 nm, and reflect the desired radiation from 240 to 280 nm which can be used alone or with optional binders and/or additives to form the reflectors in any of the embodiments described above. Examples of these attenuating materials are lanthanum oxide, yttrium oxide and ytterbium oxide. Using these reflective/attenuating materials to make a reflector, or a coating for a reflector support is the most preferred embodiment of the invention.

Adding attenuating materials as part of the reflectors does not attenuate the undesired radiation which does not hit the reflector first before reaching the target. If necessary, to further protect the target from the radiation which would otherwise impinge on the target directly from the lamp, a reflective blocking element can be used so that only reflected radiation from which the undesired radiation has been attenuated can impinge on the target. The reflective blocking element 39 is shown in FIG. 4. The reflective blocking element preferably has a simple geometric form, more preferably an optically concentrating form, and most preferably an integral form of the reflecting optics. Examples of useful shapes are a triangle (shown in FIG. 4) and a half circle. The reflective blocking element can comprise any of the reflector compositions described within this application, and may or may not be made with attenuating materials or a coating of attenuating materials. Preferably the reflective blocking element comprises an attenuating material, preferably either a liquid or solid attenuating material. It is preferred that the reflective blocking element has a diffuse reflective surface. Preferably, the blocking element is sized to occlude any direct radiation from the radiation source to the target.

FIG. 5 shows an alternative embodiment of this invention. In FIG. 5 the reflector 14 comprises a reflector support 35, a material layer 47 and a transparent support 46. The transparent support 46 is transparent to at least a portion of the radiation which impinges upon it. The reflector support 35 can comprise any of the combinations of reflective or non-reflective supports, or coatings on the supports as described above. The material layer 47 comprises one or more solid attenuating materials, or can be any of the compositions comprising attenuating materials as described for FIG. 4; however, this embodiment is particularly suited for solid attenuating materials that will not stay in place without the presence of the transparent support 46, such as a packed powder. The material layer 47 can comprise an attenuating material alone, a mixture of reflective materials and attenuating materials, or an attenuating material that also reflects the desired radiation as described in reference to FIG. 4, except that the material layer 47 can be a packed powder. If the reflector comprises separate attenuating materials and reflective materials, it is preferred that the attenuating materials are located between the reflective materials and the radiation source, so that the undesirable radiation is attenuated by the attenuating materials before the desired, e.g. germicidally-effective, radiation is reflected by the reflective materials towards the target. The material layer 47 preferably has a thickness from 0.1 to 2500 microns.

The transparent support 46, can be completely transparent to most or all of the wavelengths which impinge upon it, or the transparent support 46 can comprise a solid attenuating material which attenuates one or more of the undesired wavelengths of the radiation. Alternatively, the transparent support 46 can have a passageway through which liquid attenuating materials are pumped or otherwise held within (not shown). The transparent support 46 preferably comprises the glass, quartz or sapphire materials described above for the flow tube 13, lamp envelope 12, and/or protective window 15. The solid attenuating materials can be added to the transparent support 46 as a dopant in feed stock used to form the transparent support, or attenuating materials can be applied as a coating onto either or both sides of the transparent support 46. If the attenuating materials are applied to one side of the transparent support 46, preferably it is the side 49 furthest from the lamp. The methods for applying the coating are as described above for earlier embodiments.

Alternatively, reflective materials can be applied as a coating to the side 49 of the transparent support 46 furthest from the lamp, and the solid attenuating materials can be applied onto the other side 48 of the transparent support, if desired. In that embodiment, the material layer 47 and the reflector support 35 (as shown) might not be necessary. If present, the coatings on the transparent support 46 will preferably be from 0.1 to 2500 microns.

The preferred attenuating material for the material layer 47 used in combination with the transparent support 46 is a packed layer of powder consisting of the preferred solid attenuating materials listed above. As listed above, the most preferred solid attenuating materials are lanthanum oxide, yttrium oxide or ytterbium oxide or mixtures of these powders.

Other preferred embodiments comprise reflective materials (either coating, solid blocks or dry powder) under a coating of a solid attenuating material. The preferred combinations of reflective materials and attenuating materials in the preferred embodiments are barium sulfate (reflective material) and lanthanum oxide (attenuating material); or magnesium fluoride (reflective material) and yttrium oxide (attenuating material), or magnesium oxide (reflective material) and ytterbium oxide (attenuating material), or aluminum oxide (reflective material) and lanthanum oxide (attenuating material), or different combinations of the reflective materials and attenuating materials, or mixtures of individual reflective materials and mixtures of individual attenuating materials.

The preferred reflectors are diffuse reflectors and/or elliptically-shaped reflectors which are disclosed and described in provisional application U.S. Ser. No. 60/143,608 filed Jul. 13, 1999 "Reflectors for UV Radiation Source", U.S. Ser. No. 04/515,191, filed concurrently herewith incorporated herein by reference. The preferred lamp system comprises two lamps each having a shaped reflector, preferably an elliptically-shaped reflector, within which is a target volume (the volume occupied by the target container and/or product) having an optimized amount of space or minimal space between the target and the reflectors during the exposure of the target to radiation. The space adjacent to the target area or volume allows radiation to pass by the target without passing through the target. Therefore, particularly for a multiple lamp and/or reflector radiation system, the space should be minimized. The diffuse reflectors provide uniform energy to the target area or volume.

Figure 6:
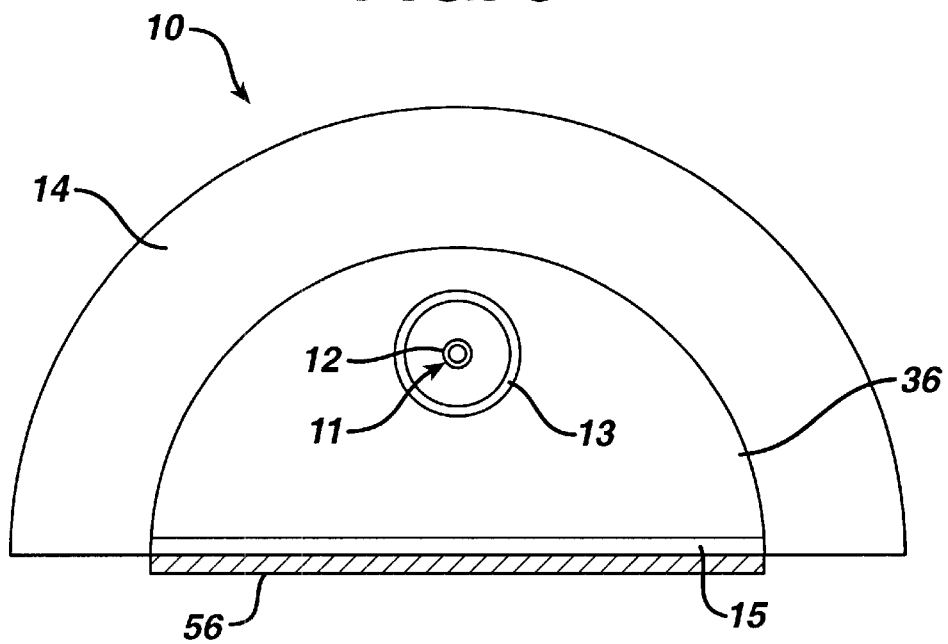
FIG. 6 shows a cross-section of another flash lamp of this invention having an attenuating material.

Another embodiment of this invention is a radiation system having a removable solid attenuating material between the radiation source and the target. FIG. 6 shows this embodiment wherein a removable solid attenuating material is a film 56 which is mounted adjacent to the protective window 15 of a flash lamp 10. (The flash lamp 10 is as shown in the earlier figures). The removable solid attenuating material 56 can comprise any of the above listed solid attenuating materials which are either combined with a binder to form a removable solid attenuating material 56, or the solid attenuating materials can be sintered with optional glass or metal oxides to form a solid, or a dry powder can be packed into a glass support. These removable solid materials 56, like the coatings, and reflectors made for the embodiments described above are very durable. The removable solid attenuating material 56 can be a block or plate. The block or plate preferably has a thickness of from 100 to 2500 microns. In another embodiment the removable solid attenuating material 56 is a sheet or film preferably comprising a polymeric material, e.g. polyamides (nylons), or polyolefins, such as polypropylene, preferably nylons such as nylon-6 and nylon-6,6. The sheet or the film may only have temporary effectiveness and may require replacement with a new or different piece or area of the removable solid attenuating material. In the preferred embodiment, the removable solid attenuating material 56 is a film which can be on rollers (not shown) which advances an exposed area of the removable solid attenuating material 56 to a never-before-exposed portion after a specified amount of exposure to the UV radiation source. The film preferably has a thickness of from 10 to 100 microns.

For embodiments in which a product to be exposed to the UV radiation is housed in a container, another alternative is to add the attenuating materials to the container or to form the container out of attenuating materials, or to add the attenuating materials to the product, or to the solution in which the product is stored, e.g. contact lens solutions. Any of the above listed attenuating materials, preferably the solid attenuating materials, can be applied to the container by all the methods described above e.g. coating, dipping, etc., or the attenuating materials can be included in the container formulation used to make the container, or the materials for the container can be selected based on their ability to attenuate the undesired radiation and transmit the desired radiation. For example, for the preferred embodiment, a container is used to house a contact lens to be sterilized. The container comprises a bowl and a lidstock. The lidstock can comprise a nylon layer and/or attenuating materials, such as lanthanum oxide, or adipic acid (hexanedioic acid) and various adipates, barium adipate, calcium adipate, magnesium adipate, disodium adipate or carboxylic acids, can be added to the molten polypropylene or polystyrene before injection molding the lidstock or the bowl. Other useful materials for the container are disclosed in Peck, et al, U.S. Ser. No. 09/259,795 entitled "Package for Medical Device" which is incorporated herein by reference.

Alternatively, attenuating materials such as polyamides (nylons) can be co-injected with the polypropylene to form a multi-layered bowl that filters out the damaging radiation.

Alternatively, attenuating materials, e.g. sol gels, can be chemically vapor deposited to the lidstock material which protects the product from UV radiation and limits water transport through the lidstock. Lanthanum oxide is an example of an attenuating material which would be useful for this purpose. Other sol gel precursors useful in the lidstock include: Barium hexafluoroacetylacetonate, Barium (2,2,6,6-tetramethyl-3,5-heptanedionate), Lanthanum acetylacetonate hydrate, Lanthanum (2,2,6,6-tetramethyl-3,5-heptanedionate), Magnesium acetylacetonate dihydrate, Magnesium (2,2,6,6-tetramethyl-3,5-heptanedionate), Ytterbium acetylacetonate, Ytterbium hexafluoroacetylacetonate, Ytterbium (2,2,6,6-tetramethyl-3,5-heptanedionate), Yttrium acetylacetonate, Yttrium hexafluoroacetylacetonate, and Yttrium (2,2,6,6-tetramethyl-3,5-heptanedionate).

The preferred attenuating materials are those that attenuate the undesired radiation and reflect, transmit or re-emit the desired radiation and have a sharp transition between the absorption of the undesired radiation and reflection, transmission or re-emission of the desired radiation. It is preferred that the change in % reflectivity/nm is greater than 2, more preferably greater than 3, most preferably greater than 4 in area of the radiation spectrum where the transition from desirable wavelengths of radiation to undesirable wavelengths of radiation is located. For the preferred embodiment in which the undesired radiation is the damaging radiation and the desired radiation is the germicidally-effective radiation, the sharp transition preferably takes place from 230 to 250 nm, more preferably from 235 to 245 nm, and most preferably from 239 to 240 nm.

Combinations of the above described embodiments are contemplated by this invention to produce an additive effect on reducing the undesired radiation, and increasing the ratio of the desired to the undesired radiation. The most preferred embodiments are the ones which use durable attenuating materials that do not have to be monitored or changed often. It is preferred that the attenuating materials can survive the application of 100 pulses at 3 $J/cm^2$, more preferred greater than 10,000 pulses, and most preferably greater than 1,000,000 pulses at 3 $J/cm^2$ total radiation before undergoing a significant change in their ability to attenuate the undesired radiation. The preferred embodiments are to add solid attenuating materials to the lamp envelope and/or flow tube around the lamp envelope, or to add the attenuating materials as a coating to the reflector.

This invention will be further illustrated by the following example.

EXAMPLE 1

Treated Lenses

−1.00D Acuvue® (Etafilcon A) contact lenses each in polypropylene bowls with 500 μl of borate buffered saline solution, and a clear lidstock heat-sealed to the bowl were placed six at a time into the cavity of a PurePulse bright light system. The lenses in the containers were subjected to 4 flashes, from two xenon flash lamps flashing simultaneously, to provide about 12 $J/cm^2$ radiation from 200–3000 nm of which about 850mJ/$cm^2$ was radiation from 240 to 280 nm. The contact lenses were tested for water content both by refractive index and GRAVIMETRIC methods. The modulus and base curve were also measured. The measurements are in Table 2.

Treated Lenses with Attenuating Material

−1.00D Acuvue® contact lenses packaged as described above were treated as described above, except that a piece of 12 μm thick nylon film was placed beneath the containers on the bowl side of the containers.

The same measurements as described above were taken. The measurements are in Table 2.

Untreated Lenses

Measurements of the characteristics of 48 untreated −1.00D Acuvue Lenses were also made. They are listed in Table 2.

TABLE 2

| CHARACTERISTICS | UN-TREATED LENSES | TREATED LENSES | TREATED LENSES W/ATTENUATING MATERIAL |
|---|---|---|---|
| DOSE (mJ/$cm^2$ @ 240 to 280 nm) | NONE | 850 | 850 |
| NYLON FILM | NO | NO | YES |
| BASE CURVE (mm) | 8.82 | 8.79 | 8.82 |
| MODULUS (psi) | 42.3 | 36.3 | 40.2 |
| WATER (%) RI | 58.4 | 59.5 | 58.9 |
| WATER (%) GRAV | 59.5 | 60.2 | 59.6 |

This example shows that the nylon attenuates the undesired radiation and partially protects the contact lens polymer from damage.

EXAMPLE 2

Treated Lenses without Attenuating Material

Acuvue® (Etafilcon A) contact lenses each in polypropylene bowls with 500 μl of borate buffered saline solution, and a clear lidstock heatsealed to the bowl were placed into the cavity of a PurePulse bright light system. The lenses in the containers were subjected to various amounts of energy provided by two xenon flash lamps flashing simultaneously. The water content of the bowl side of the contact lenses was measured by the Abbe method after treatment at different energy levels. (Each point on the graph represents the average measurement for ten contact lenses.) These measurements are plotted in FIG. 7.

Treated Lenses with Attenuating Material

Acuvue® contact lenses packaged as described above were treated as described above, except that instead of using the specular polished aluminum PurePulse reflectors in the cavity, the specular reflectors were coated with 30 coats of barium sulfate and 10 coats of lanthanum oxide over the barium sulfate. The coating materials were spray coated at room temperature and dried between the application of each coat. The barium sulfate coating consisted of a 1:1:0.1 weight ratio of barium sulfate, water and sodium silicate. The lanthanum oxide coating consisted of a 1:1:0.1 weight ratio of lanthanum oxide, water and sodium silicate. The same measurements as described above were repeated for the contact lenses treated by the system having reflectors with attenuating materials. These measurements are plotted in FIG. 7.

Figure 7:
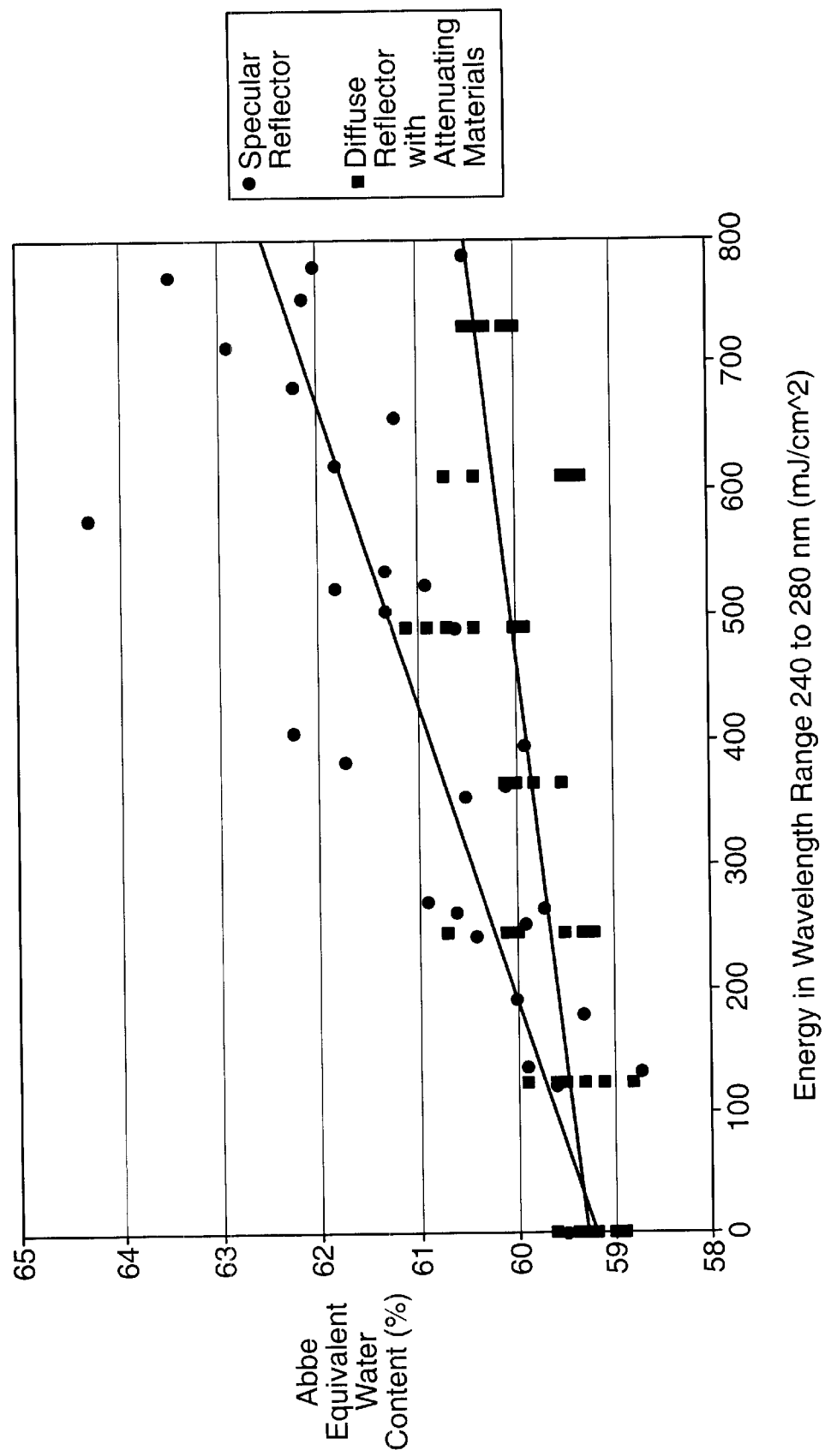
FIG. 7 is a graph of the Equilibrium Water Content of a contact lens polymer as function of the radiation dose to the polymer for systems with and without attenuating materials of this invention.

FIG. 7 shows that the attenuating coating on the reflectors protects the contact lenses from damage, which is evidenced by the decreased change in equilibrium water content for the contact lenses when treated with a system having attenuating materials in the reflectors as compared to the system without the attenuating material in the reflectors.

Comparative Example

The materials in Table 3 were measured the same way as the materials in Table 1. These materials would not be useful as attenuating materials in this invention.

TABLE 3

| Material | Observed Visual Color | % R Mean 200–400 | % R Std Dev 200–400 | % R Mean 240–280 | % R Std Dev 240–280 | % R Mean 200–240 | % R Std Dev 200–240 |
|---|---|---|---|---|---|---|---|
| Praseodymium Oxide | Black | 13.67 | 5.59 | 12.13 | 0.33 | 20.7 | 9.49 |
| Titanium Dioxide | White | 14.92 | 5.17 | 13.12 | 0.28 | 20.75 | 9.14 |
| Zinc Oxide | White | 15.85 | 13.39 | 10.99 | 0.35 | 20.72 | 11.36 |

This invention has been described in reference to particular embodiment, alternate embodiments are know to persons of ordinary skill in the art and fall within the scope of the claims which follow.

What is claimed is:

1. A high energy radiation system comprising a UV radiation source, wherein said apparatus comprises a selectively attenuating material which increases the ratio of desired to undesired radiation to reduce the radiation damage to a target by selectively attenuating at least 30 percent of the radiation from greater than 200 nm up to 240 nm which impinges upon said attenuating material, and directs greater than 50 percent of the radiation from 240 nm to 280 nm which impinges upon said attenuating material.

2. The system of claim 1, wherein said selectively attenuated radiation is from 100 nm up to 240 nm.

3. The system of claim 1, wherein said selectively attenuated radiation is from 180 nm up to 240 nm.

4. The system of claim 3, wherein said system selectively attenuates at least 60 percent of the radiation from 180 nm up to 240 nm.

5. The system of claim 3, wherein said system selectively attenuates at least 90 percent of the radiation from 180 nm up to 240 nm.

6. The system of claim 1, wherein said system selectively attenuates greater than 90 percent of the radiation, greater than 200 nm up to 240 nm.

7. The system of claim 1, wherein said system directs greater than 75 percent of the radiation from 240 nm to 280 nm.

8. The system of claim 4, wherein said system directs greater than 75 percent of the radiation from 240 nm to 280 nm.

9. The system of claim 4, wherein said system directs greater than 90 percent of the radiation from 240 nm to 280 nm.

10. The system of claim 2, wherein said system directs greater than 90 percent of the radiation from 240 nm to 280 nm, and wherein said system selectively attenuates at least 90 percent of the radiation from 100 nm up to 240 nm.

11. The system of claim 1, wherein said attenuating material has an attenuation ratio of 1.2.

12. The system of claim 3, wherein said attenuating material has an attenuation ratio of 1.8.

13. The system of claim 1, wherein said attenuating material comprises a gas.

14. The system of claim 1, wherein said attenuating material comprises a liquid.

15. The system of claim 14, wherein said liquid is selected from the group consisting of polyols, halogenated carbon compounds, organic carbonates, silicon compounds, mixtures of said liquids, and a solid attenuating material in a liquid carrier.

16. The system of claim 14, wherein said liquid is selected from the group consisting of alkyl alcohols, propylene glycols having a weight average molecular weight from 200 to 1,000, fluorocarbons, chlorocarbons, chloroform, fully halogenated carbon compounds, freon, fluorinerts, fluorinerts having nitrogen within their compositions, aliphatic carbonates, propylene carbonates, sodium silicate, polysiloxane compounds, polydimethylsiloxanes, hydride-terminated silicone oil, and mixtures of said liquids.

17. The system of claim 14, wherein said liquid comprises chloroform and propylene carbonate.

18. The system of claim 15, wherein the location of said liquid attenuating material is selected from the group consisting of between a lamp envelope and a flow tube, between a flow tube and a protective window, and within a passageway adjacent to a reflector, within a passageway adjacent a protective window, and within a passageway located between a target and said radiation source.

19. The system of claim 1, wherein said attenuating material comprises a solid.

20. The system of claim 19, wherein said solid is selected from the group consisting of alkaline metal compounds, heavy metal oxides, divalent metal oxides, and polyvalent metal oxides, rare earth metal oxides, rare earth metal halides, and metallic combination oxides.

21. The system of claim 19, wherein said solid comprises $M_aO_bX_cH_d$ wherein M is a single metal or a mix of metals, O is oxygen, X is a heteroatom, and H is a halide, a is 1 to 20, b is 0 to 20, c is 0 to 20, and d is 0 to 20, with the proviso that at least b, c or d is at least 1.

22. The system of claim 19, wherein said solid material is more than 99.9% pure.

23. The system of claim 19, wherein said solid material is selected from the group consisting of calcium oxide, hafnium oxide, lanthanum oxide, iron oxide, terbium oxide, praseodymium oxide, barium titanate. magnesium fluoride, magnesium oxide, aluminum oxide, barium oxide, barium titanate, holmium oxide, calcium oxide, lanthanum oxide, germanium oxide, tellurium oxide, europium oxide, erbium oxide, neodymium oxide, samarium oxide, ytterbium oxide, yttrium oxide, and dysprosium oxide.

24. The system of claim 19, wherein said solid material is selected from the group consisting of magnesium oxide, erbium oxide, holmium oxide, samarium oxide, tellurium oxide, lanthanum oxide, yttrium oxide, and ytterbium oxide.

25. The system of claim 19, wherein said solid material is selected from the group consisting of lanthanum oxide, yttrium oxide, and ytterbium oxide.

26. The system of claim 3, wherein said attenuating material is a solid attenuating material incorporated as a dopant into said system in a lamp envelope, protective window, flow tube, reflector, passageway, transparent support, blocking element or removable solid material.

27. The system of claim 3, wherein said attenuating material is a solid attenuating material incorporated as a coating into said system on a lamp envelope, protective window, flow tube, reflector, passageway, transparent support, blocking element or removable solid material.

28. The system of claim 27, wherein said coating can be applied by painting, spraying, plasma coating, dipping, casting, conversion coating, gel coating, etching, chemical vapor depositing, sputtering, or chemical or mechanical bonding.

29. The system of claim 19, wherein said solid attenuating materials comprise materials selected from the group consisting of polyvinyl alcohols, cyanoacrylates, acrylics, silicones.

30. The system of claim 29, wherein said solid attenuating materials comprise materials selected from the group consisting of sodium silicate, low-temperature sintered glasses, alkali oxide silicates, sodium, potassium and lithium silicates, sol gel binder precursors, aluminum tert butoxide, sodium silicate, tetraethylorthosilicate (TEOS), metal isopropoxides, dysprosium ethylhexano-diisopropoxide in isopropanol, dysprosium 2-ethylhexanoate in hexane, dysprosium isopropoxide in toluene-isopropanol, dysprosium 2-methoxyethoxide in 2-methoxyethanol, erbium ethylhexano-diisopropoxide in isopropanol, erbium 2-ethylhexanoate in hexane, erbium isopropoxide in toluene-isopropanol, holmium ethylhexano-diisopropoxide in isopropanol, holmium isopropoxide in toluene-isopropanol, holmium 2-methoxyethoxide in 2-methoxyethanol, lanthanum acetate, lanthanum 2-ethylhexanoate in hexane, lanthanum isopropoxide, lanthanum 2-methoxyethoxide in 2-methoxyethanol, magnesium ethoxide in ethanol, magnesium methoxide in methanol, magnesium 2-methoxyethoxide in 2-methoxyethanol, neodymium ethylhexano-diisopropoxide in isopropanol, neodymium 2-ethylhexanoate in hexane, neodymium isopropoxide in toluene-isopropanol, neodymium 2-methoxyethoxide in 2-methoxyethanol, samarium ethylhexano-monoisopropoxide in toluene isopropanol, samarium 2-ethylhexanoate in hexane, samarium isopropoxide in toluene-isopropanol, samarium 2-methoxyethoxide in 2-methoxyethanol, ytterbium isopropoxide in toluene-isopropanol, ytterbium 2-methoxyethoxide in 2-methoxyethanol, yttrium ethylhexano-diisopropoxide in toluene-isopropanol, and yttrium ethylhexano-monoisopropoxide in toluene-isopropanol.

31. The system of claim 29, wherein said solid attenuating materials comprise materials selected from the group consisting of lanthanum acetate, lanthanum 2-ethylhexanoate in hexane, lanthanum isopropoxide, lanthanum 2-methoxyethoxide in 2-methoxyethanol, ytterbium isopropoxide in toluene-isopropanol, ytterbium 2-methoxyethhoxide in 2-methoxyethanol, ytterbium ethylhexano-diisopropoxide in toluene-isopropanol, and yttrium ethylhexano-monoisopropoxide in toluene-isopropanol.

32. The system of claim 27, wherein the thickness of the attenuating coatings is between from 0.1 to 2500 microns.

33. The system of claim 1, wherein said reflector further comprises a reflective material selected from the group consisting of polished aluminum, barium sulfate, aluminum oxide, magnesium fluoride, and magnesium oxide.

34. The system of claim 1, wherein said reflector comprises barium sulfate and lanthanum oxide.

35. The system of claim 1, wherein the reflector 14 can be machined out of the formed solid which comprises the reflector materials, and attenuating materials.

36. The system of claim 34, wherein said attenuating material is selected from the group consisting of lanthanum oxide, yttrium oxide and ytterbium oxide.

37. The system of claim 1 further comprising a blocking element.

38. The system of claim 37, wherein said blocking element comprises said attenuating material, and has a diffuse reflective surface.

39. The system of claim 1, wherein no direct radiation from said radiation source impinges a target.

40. The system of claim 1 further comprising at least one reflector for said radiation source, wherein said reflector is a diffuse reflector having an elliptical shape.

41. The system of claim 1 further comprising a removable solid material comprising said selectively attenuated material, said solid material being located between the radiation source and the target.

42. The system of claim 41, wherein said removable solid material has the form selected from the group consisting of a film, block, plate, and powder packed into a support.

43. The system of claim 42, wherein said film comprises a polymeric material selected from the group consisting of polyamides and polyolefins.

44. The system of claim 1, wherein said system further comprises a target wherein said target comprises said attenuating materials.

45. The system of claim 44, wherein said target comprises a material selected from the group consisting of nylon, lanthanum oxide, adipic acid, barium adipate, calcium adipate, magnesium adipate, disodium adipate, carboxylic acids, and sol gels precursors.

46. The system of claim 44, wherein said target further comprises a container and a product, wherein said container comprises a material selected from the group consisting of Barium hexafluoroacetylacetonate, Barium (2,2,6,6-tetramethyl-3,5-heptanedionate, Lanthanum acetylacetonate hydrate, Lanthanum (2,2,6,6-tetramethyl-3,5-heptanedionate, Magnesium acetylacetonate dihydrate, Magnesium (2,2,6,6-tetramethyl-3,5-heptanedionate), Ytterbium acetylacetonate, Ytterbium hexafluoroacetylacetonate, Ytterbium (2,2,6,6-tetramethyl-3,5-heptanedionate, Yttrium acetylacetonate, Yttrium hexafluoroacetylacetonate, and Yttrium (2,2,6,6-tetramethyl-3,5-heptanedionate.

47. The system of claim 1, wherein said attenuating material undergoes a change in % reflectivity/nm greater than 2, between from 230 to 250 nm.

48. The system of claim 1, wherein said attenuating material undergoes a change in % reflectivity/nm greater than 3, between from 235 to 245 nm.

49. A high energy radiation system comprising a UV radiation source, wherein said apparatus comprises a selectively attenuating material which increases the ratio of desired to undesired radiation to reduce the radiation damage to a target by selectively attenuating at least 30 percent of the radiation from greater than 200 nm up to 250 nm which impinges upon said attenuating material, and directs greater than 50 percent of the radiation from 250 nm to 280 nm which impinges upon said attenuating material.

* * * * *